United States Patent [19]

Kuwata et al.

[11] Patent Number: 5,788,884
[45] Date of Patent: Aug. 4, 1998

[54] OIL-IN-WATER ORGANOPOLYSILOXANE EMULSION AND METHOD FOR THE PREPARATION THEREOF

[75] Inventors: Satoshi Kuwata; Morizo Nakazato; Hideki Hagiwara; Teruki Ikeda, all of Gunma-ken, Japan

[73] Assignee: Shin-Etsu Chemical Co., Ltd., Tokyo, Japan

[21] Appl. No.: 827,447

[22] Filed: Mar. 28, 1997

[30] Foreign Application Priority Data

Mar. 29, 1996 [JP] Japan ................... 8-076055

[51] Int. Cl.$^6$ ................... B01J 13/00; A61K 7/075; A61K 7/08
[52] U.S. Cl. ................... 252/312; 252/314; 424/70.12; 424/70.28; 424/401; 510/122; 510/417
[58] Field of Search ................... 252/312, 314; 424/70.12, 70.28, 401; 510/122

[56] References Cited

U.S. PATENT DOCUMENTS

| Re. 34,584 | 4/1994 | Grote et al. | 510/122 |
|---|---|---|---|
| 3,208,911 | 9/1965 | Oppliger | 424/70.12 |
| 3,964,500 | 6/1976 | Drakoff | 424/70.12 X |
| 4,472,375 | 9/1984 | Bolich, Jr. et al. | 424/70.12 |
| 4,493,824 | 1/1985 | Abe | 424/70.12 |
| 4,704,272 | 11/1987 | Oh et al. | 424/70.28 X |
| 4,741,855 | 5/1988 | Grote et al. | 252/312 X |
| 4,784,665 | 11/1988 | Ona et al. | 252/312 X |
| 4,814,376 | 3/1989 | Tanaka et al. | 252/314 X |
| 5,286,476 | 2/1994 | Nanba et al. | 424/70.12 X |
| 5,302,658 | 4/1994 | Gee et al. | 252/312 X |
| 5,415,860 | 5/1995 | Beucherie et al. | 424/70.12 X |
| 5,500,148 | 3/1996 | Ohba et al. | 252/315.2 |
| 5,714,446 | 2/1998 | Bartz et al. | 510/122 X |

*Primary Examiner*—Richard D. Lovering
*Attorney, Agent, or Firm*—Millen, White, Zelano, & Branigan, P.C.

[57] ABSTRACT

A novel aqueous organopolysiloxane emulsion composition of the oil-in-water type suitable as an additive ingredient in toiletry preparations for hair-care treatment, of which the organopolysiloxane particles have a relatively large volume-average particle diameter of 3 to 100 μm as emulsified by using a quaternary ammonium chloride as a cationic surface active agent. The emulsion composition is advantageous in respect of the improved stability of the emulsion and increased retention on the hair treated with the hair-care composition. The emulsion composition is prepared in a process comprising the steps of: mixing the organopolysiloxane and the cationic surface active agent with a relatively small volume of water; vigorously agitating the mixture so as to cause phase inversion into an oil-in-water base emulsion; and diluting the base emulsion with an additional volume of water, optionally, containing the cationic surface active agent.

27 Claims, No Drawings

OIL-IN-WATER ORGANOPOLYSILOXANE EMULSION AND METHOD FOR THE PREPARATION THEREOF

BACKGROUND OF THE INVENTION

The present invention relates to a novel aqueous organopolysiloxane emulsion of the oil-in-water type and a method for the preparation thereof. More particularly, the invention relates to an oil-in-water aqueous emulsion of an organopolysiloxane useful as an additive in or as a base material of various kinds of toiletry and cosmetic compositions such as hair-care compositions, e.g., hair rinses, hair conditioners, hair treatment agents and the like, lustering polishes, mold release agents, fiber finishing agents and so on as well as an efficient method for the preparation thereof.

As is well known, aqueous organopolysiloxane emulsions are used in a wide variety of applications as an additive in or as a base material in the preparation of a great variety of hair-care compositions, polishes, mold release agents, fiber finishing agents and the like. For example, a proposal is made in Japanese Patent Kokai 4-36226 and 4-224309 for a formulation of shampoo compositions with admixture of an aqueous organopolysiloxane emulsion, in which it is taught that the particle diameter of the organopolysiloxane particles or droplets dispersed in the emulsion is preferably 2 μm or smaller to ensure that the foamability of the shampoo composition is never decreased by the addition thereof.

It is also proposed in Japanese Patent Kokai 63-130512, 513994 and 5-163122 to admix a hair-care preparation with an aqueous organopolysiloxane emulsion which is a so-called microemulsion containing the organopolysiloxane in the form of extremely fine particles. Such a hair-care composition compounded with an organopolysiloxane emulsion of which the particle diameter of the emulsified organopolysiloxane is relatively small has a problem that the organopolysiloxane particles exhibit only poor adhesion onto the hair so that they are readily washed away from the hair and do not give a persistent effect.

In view of these problems, the inventors have proposed, in Japanese Patent Kokai 7-188557, an aqueous organopolysiloxane emulsion suitable as an ingredient in a hair-care composition, in which the organopolysiloxane particles have a relatively large diameter of 3 to 100 μm. In fact, a considerable improvement can be obtained by the use of such an aqueous organopolysiloxane emulsion as an additive in shampoo compositions at least in relation to the adhesion of the organopolysiloxane particles to the hair.

Although the above mentioned organopolysiloxane emulsion is suitable as an additive ingredient in shampoo compositions usually in the form of an anionic emulsion, the emulsion cannot be used in a cationic hair-care composition such as hair rinses, hair conditioners, hair treatment agents and the like since they do not give a stable product because admixture of an anionic organopolysiloxane emulsion in a cationic hair-care composition results in separation of the organopolysiloxane from the emulsion or formation of precipitates. It is accordingly desired to develop a cationic aqueous emulsion of an organopolysiloxane of which the organopolysiloxane particles have a relatively large particle diameter.

SUMMARY OF THE INVENTION

The present invention accordingly has an object, in view of the above described problems and disadvantages in the conventional aqueous organopolysiloxane emulsions in the prior art, to provide a novel and improved aqueous organopolysiloxane emulsion composition of the oil-in-water type as well as a method for the preparation thereof.

Thus, the oil-in-water aqueous organopolysiloxane emulsion composition of the present invention is a uniform dispersion which comprises:

(A) 100 parts by weight of an organopolysiloxane having a viscosity in the range from 100 to 5,000,000 centipoise at 25° C. represented by the average unit formula

$$R_a SiO_{(4-a)/2}, \qquad (I)$$

in which R denotes a monovalent organic group having 1 to 20 carbon atoms, which is preferably an unsubstituted or substituted monovalent hydrocarbon group or, more preferably, a methyl group or phenyl group, and the subscript a is a positive number in the range from 1.8 to 2.2;

(B) from 0.5 to 30 parts by weight of a cationic surface active agent which is preferably a quaternary ammonium compound represented by the general formula

$$[R^1_4 N]^+ \cdot X^-, \qquad (II)$$

in which at least one of the four groups denoted by $R^1$ is an alkyl or alkenyl group having 8 to 28 carbon atoms, each of the remaining groups denoted by $R^1$, if any, is, independently from the others, a benzyl group or an alkyl group having 1 to 5 carbon atoms and $X^-$ denotes a halogen anion or an organic anion; and (C) from 10 to 300 parts by weight of water as a dispersion medium of the components (A) and (B), the component (A) being dispersed in the component (C) in the form of particles having a volume-average particle diameter in the range from 3 to 100 μm.

The particle size distribution of the organopolysiloxane particles relative to the volume-average particle diameter preferably follows a normal or Gaussian distribution function with broadness defined by a parameter α, which is the ratio of the standard deviation to the volume-average particle diameter, in the range from 0.1 to 1.0.

It is preferable that the organopolysiloxane as the component (A) having the above specified viscosity is a mixture of two organopolysiloxanes having different viscosities each from the other, of which the first organopolysiloxane has a viscosity in the range from 10 to 1000 centipoise at 25° C. and the second organopolysiloxane has a viscosity in the range from 5,000,000 to 20,000,000 centipoise at 25 ° C. in such a proportion that the resultant mixture has a viscosity in the range from 1000 to 3,000,000 centipoise at 25° C.

The oil-in-water aqueous organopolysiloxane emulsion composition defined above can be prepared from the components (A), (B) and (C) in a process which comprises the steps of:

(a) mixing 100 parts by weight of the organopolysiloxane as the component (A) defined above, from 0.5 to 30 parts by weight of the cationic surface active agent as the component (B) as defined above and from 1 to 30 parts by weight of water as the component (C) to form a base emulsion of the water-in-oil type;

(b) agitating the water-in-oil emulsion to form an oil-in-water base emulsion by phase inversion; and (c) diluting the oil-in-water base emulsion with water in an additional amount of at least 20% or, preferably, at least 30% of the amount of water used in step (a) to make up a total amount of water in the range from 10 to 300 parts by weight.

DETAILED DESCRIPTION OF THE PREFERRED EMBODIMENTS

The principal ingredient in the inventive oil-in-water aqueous emulsion is the organopolysiloxane as the component (A) represented by the average unit formula (I) given above. The group denoted by R in the formula is a monovalent organic group having 1 to 20 carbon atoms including unsubstituted or substituted monovalent hydrocarbon groups exemplified by alkyl groups such as methyl, ethyl, propyl, butyl, pentyl, hexyl, octyl, decyl, dodecyl, tetradecyl, hexadecyl and octadecyl groups, aryl groups such as phenyl and tolyl groups, cycloalkyl groups such as cyclopentyl and cyclohexyl groups and halogen-substituted alkyl groups such as 3,3,3-trifluoropropyl, 2-(perfluoro-n-butyl)ethyl and 2-(perfluoron-octyl)ethyl groups as well as organic groups having an epoxy, amino, mercapto, acyloxy, methacryloxy, alkyl carboxylate, carboxyl, hydroxyl or ether group, of which preferable are the unsubstituted monovalent hydrocarbon groups and more preferable are methyl and phenyl groups. In particular, it is most preferable that all or at least 50% in number of the groups denoted by R are methyl groups.

Although the organopolysiloxane as the component (A) is constituted basically from high molecular-weight species such as, preferably, non-volatile dimethylpolysiloxanes and methyl-phenylpolysiloxanes of a high degree of polymerization, it is optional or sometimes preferable depending on the particularly intended application of the emulsion composition that the component (A) is a mixture of two organopolysiloxanes having different viscosities each from the other, of which the first non-volatile organopolysiloxane has a viscosity in the range from 10 to 1000 centipoise at 25° C. and the second non-volatile organopolysiloxane has a viscosity in the range from 5,000,000 to 20,000,000 centipoise at 25° C. in such a proportion that the resultant mixture has a viscosity in the range from 1000 to 3,000,000 centipoise at 25° C. The organopolysiloxane as the component (A) further can be a mixture of a high molecular-weight non-volatile organopolysiloxane having a viscosity in the range from 5,000,000 to 20,000,000 centipoise at 25° C. and a low molecular-weight volatile organopolysiloxane of a cyclic or linear molecular structure having a boiling point in the range from 100° to 250° C. under normal pressure.

The organopolysiloxane as the component (A) should have a viscosity at 25° C. in the range from 100 to 5,000,000 centipoise or, preferably, from 1000 to 3,000,000 centipoise or, more preferably, from 10,000 to 1,000,000 centipoise. When the viscosity of the component (A) is too low, the emulsion composition prepared from the organopolysiloxane can hardly exhibit the desired effects of hair conditioning, mold releasing, lustering as a polish, lubricity as a lubricant and so on while, when the viscosity thereof is too high, the aqueous emulsion obtained therefrom would suffer a decrease in the stability of the emulsion. A typical example of the organopolysiloxane as the component (A) is obtained by dissolving a high molecular-weight dimethylpolysiloxane having a viscosity in the range from 5,000,000 to 20,000,000 centipoise and a low molecular weight dimethylpolysiloxane having a viscosity in the range from 10 to 1000 centipoise each at 25° C. in such a weight proportion that the resultant mixture may have a viscosity in the range from 1000 to 3,000,000 centipoise or, more preferably, from 10,000 to 1,000,000 centipoise at 25° C.

The component (B) in the inventive aqueous emulsion composition is a cationic surface active agent to serve as an emulsifying agent for the organopolysiloxane as the component (A). Suitable cationic surface active agent includes quaternary ammonium compounds exemplified by higher-alkyl trimethyl ammonium salts such as lauryl trimethyl ammonium chloride, cetyl trimethyl ammonium chloride and stearyl trimethyl ammonium chloride and higher-alkyl dimethyl benzyl ammonium salts such as lauryl dimethyl benzyl ammonium chloride, cetyl dimethyl benzyl ammonium chloride and stearyl dimethyl benzyl ammonium chloride, adducts of an alkyl amine and ethylene oxide such as dihydroxyethyl stearyl amine, salts of an amine compound such as triethanolamine monostearate formate and stearamidoethyl diethyl amine acetate, surface active agents of the imidazoline type such as 2-heptadecenyl hydroxyethyl imidazoline and pyridinium salts such as cetyl pyridinium chloride and stearamidomethyl pyridinium chloride. These cationic surface active agents can be used either singly or as a combination of two kinds or more according to need. Preferably, the cationic surface active agent as the component (B) is a quaternary ammonium compound represented by the general formula $$[R^1{}_4N]^+ \cdot X^-, \qquad (II)$$

in which at least one of the four groups denoted by $R^1$ is an alkyl or alkenyl group having 8 to 28 carbon atoms, each of the remaining groups denoted by $R^1$, if any, is, independently from the others, a benzyl group or an alkyl group having 1 to 5 carbon atoms and $X^-$ denotes a halogen anion or an organic anion. Examples of the quaternary ammonium compounds include the above named chlorides for the compounds in which the anion is a chlorine anion and lauryl trimethyl ammonium methosulfate, cetyl trimethyl ammonium methosulfate and stearyl trimethyl ammonium methosulfate for the compounds in which the anion is an organic anion.

The amount of the cationic surface active agent as the component (B) in the inventive emulsion composition is in the range from 0.1 to 30 parts by weight or, preferably, from 1 to 20 parts by weight or, more preferably, from 2 to 10 parts by weight per 100 parts by weight of the organopolysiloxane as the component (A). In the preparation of the inventive emulsion composition, the component (B) is admixed with the component (A) preferably in the form of an aqueous solution. Commercial products of quaternary ammonium salts, which are available only in the form of an aqueous solution, are suitable for the purpose.

The component (C) in the aqueous emulsion composition of the invention is water which serves as a dispersion medium of the above described components (A) and (B). The amount of the water in the inventive emulsion composition is in the range from 10 to 300 parts by weight per 100 parts by weight of the organopolysiloxane as the component (A) though dependent on the intended application of the emulsion composition. When the amount of water is too large, the content of the organopolysiloxane in the emulsion composition is so low that the aqueous emulsion cannot have sufficiently high stability of the emulsion while, when the amount of water is too small, the emulsion composition is so thick and has an unduly high viscosity to cause inconvenience in handling. The content of water as the component (C) in the inventive aqueous emulsion composition should be in the range from 10 to 300 parts by weight or, preferably, from 15 to 100 parts by weight or, more preferably, from 20 to 50 parts by weight.per 100 parts by weight of the organopolysiloxane as the component (A).

The aqueous organopolysiloxane emulsion composition of the invention consisting of the above described essential ingredients including the components (A), (B) and (C) is prepared in the following manner. Thus, 100 parts by weight of the organopolysiloxane as the component (A), from 0.5 to 30 parts by weight of the cationic surface active agent as the component (B) and from 1 to 30 parts by weight of water as a part of the component (C) are blended together to form a water-in-oil emulsion which is then vigorously agitated under a high shearing force so that the phenomenon of phase inversion takes place from the water-in-oil emulsion into an oil-in-water emulsion followed by further continued agitation of the emulsion also under the high shearing force for a length of time of 30 minutes to 2 hours at a temperature of 0° C. to 50° C. to give a base emulsion. When the amount of the cationic surface active agent is too small, the phase inversion of the emulsion cannot take place. Phase inversion of the emulsion also cannot take place when the amount of water as a part of the component (C) is too small while, when the amount of water is too large, a decrease is caused in the stability of the oil-in-water emulsion formed by the phase inversion. The machine for emulsification is not particularly limitative provided that a shearing force sufficiently high for phase inversion can be obtained useful machines include Ultramixers (trade names by Mizuho Ind. Co.), Planetary Mixers, Tri-Mixes, Twin-Mixes (each a trade name by Inoue Mfg., Inc.), Combi-Mixers, Agihomo Mixers, High-vis Disperse-Mixes (each a trade name by Tokushu Kika Kogyo Co.) and the like.

The thus obtained oil-in-water base emulsion is thereafter diluted uniformly with admixture of an additional amount of water so as to make up a total amount of water in the range from 10 to 300 parts by weight per 100 parts by weight of the organopolysiloxane as the component (A). The amount of this additional portion of water should be at least 20% or, preferably, at least 30% of the water already contained in the base emulsion. If necessary, the water for dilution may contain the cationic surface active agent in the form of an aqueous solution as a supplemental portion of the component (B) although the total amount of the component (B) thus made up should not exceed 30 parts by weight per 100 parts by weight of the organopolysiloxane as the component (A) since, when the total amount of the cationic surface active agent is too large, the stability of the aqueous emulsion is also decreased.

In the oil-in-water organopolysiloxane emulsion obtained in the above described manner, the particles of the organopolysiloxane as the dispersed phase should have an average particle diameter or, in particular, volume-average particle diameter in the range from 3 to 100 µm or, preferably, from 10 to 50 µm. When the average particle diameter of the organopolysiloxane particles is too large, the aqueous emulsion is not sufficiently stable to cause separation of the oily phase while, when the particle diameter is too small, the emulsion is not suitable as an additive in a hair-care composition such as hair rinses, hair conditioners and hair treatment agents because of a decrease in the adhesion of the organopolysiloxane droplets onto the hair. It is desirable that the particle size distribution of the organopolysiloxane droplets relative to the volume-average particle diameter follows a normal or Gaussian distribution function in which the parameter $\alpha$, i.e. the standard deviation divided by the volume-average particle diameter, is in the range from 0.1 to 1.0 or, preferably from 0.3 to 0.8.

Besides the above described essential ingredients including the components (A), (B) and (C), it is optional according to the particularly intended application of the emulsion composition that the inventive aqueous emulsion composition is further admixed with various kinds of known additives such as non-ionic surface active agents, amphoteric surface active agents, thickening agents, antiseptic agents or preservatives, coloring agents, i.e. dyes and pigments, and the like each in a limited amount.

In the following, the oil-in-water aqueous organopolysiloxane emulsion composition of the invention as well as the method for the preparation thereof are illustrated in more detail by way of Examples and Comparative Examples, in which the term of "parts" always refers to "parts by weight" and the values of viscosity were all obtained at 25° C.

EXAMPLE 1

Into a stainless steel high-shearing emulsifying machine of 5 liters capacity (Model TK Combi-Mix M, manufactured by Tokushu Kika Kogyo Co.) equipped with an anchor-blade stirrer capable of agitating the whole volume of the content in the vessel and a disk stirrer having a number of tooth-formed small protrusions on each of the upper and lower disks at alternately opposite positions in the peripheral zone, were introduced 100 parts of an organopolysiloxane having a viscosity of 500,000 centipoise, which was a 40:60 by weight mixture of a first dimethylpolysiloxane having a viscosity of 15,000,000 centipoise and a second dimethylpolysiloxane having a viscosity of 200 centipoise, and 26.7 parts of an aqueous solution containing 30% by weight of cetyl trimethyl ammonium chloride and they were agitated therein for 30 minutes with the anchor-blade stirrer and disk stirrer rotated at 40 rpm and 1500 rpm, respectively, so that phase inversion took place from the initial water-in-oil emulsion to an oil-in-water base emulsion. With rotation of the disk stirrer interrupted, the base emulsion in the machine vessel was admixed and uniformly diluted with 6.7 parts of water under agitation with the anchor-blade stirrer alone to give an oil-in-water emulsion composition according to the invention, in which the total amounts of the cationic surface active agent and water were 8.0 parts and 25.4 parts, respectively, per 100 parts of the organopolysiloxane.

The thus prepared aqueous emulsion was subjected to the measurement of the volume-average particle diameter of the organopolysiloxane particles and distribution of the volume-average particle diameter by using a Coulter Counter (Model TA-11, a trade name by Coulter Electronics Co.) to find that the volume-average particle diameter was about 46 µm and the distribution of the volume-average particle diameter approximately followed a normal distribution with a value of the parameter $\alpha$ equal to 0.77.

Further, the emulsion composition was evaluated for the stability of emulsion in a testing procedure in which visual inspection was conducted of the condition of a 100 g portion of the emulsion after standing still for 30 days at 45° C. to record the results in three ratings of: A for absence of any noticeable changes; B for appearance of a small volume of a layer on or below the emulsion as formed by phase separation; and C for complete separation into two layers. The result in this Example was rated A.

EXAMPLE 2

The procedure for the preparation of a second oil-in-water organopolysiloxane emulsion composition was about the same as in Example 1 except that the initial charge to the emulsifying machine for the preparation of the base emulsion consisted of 100 parts of the same dimethylpolysiloxane, 5.3 parts of the 30% aqueous solution of the same cationic surface active agent and 13.3 parts of purified water and that 6.7 parts of water for dilution of the base emulsion were replaced with 14.7 parts of the same aqueous solution of the cationic surface active agent as used above. The total amounts of the cationic surface active agent and water were 6.0 parts and 27.3 parts, respectively, per 100 parts of the organopolysiloxane.

The volume-average particle diameter of the organopolysiloxane particles was about 30 µm and the distribution of the volume-average particle diameter followed approximately a normal distribution with the value of the parameter α equal to 0.46. The storage stability of the emulsion was rated A.

EXAMPLE 3

The procedure for the preparation of a third oil-in-water organopolysiloxane emulsion composition was substantially the same as in Example 1 excepting for the replacement of 26.7 parts of the 30% by weight aqueous solution of cetyl trimethyl ammonium chloride with 13.3 parts of a 30% by weight aqueous solution of lauryl trimethyl ammonium chloride and increase of the amount of water for dilution of the base emulsion from 6.7 parts to 20.0 parts. The total amounts of the cationic surface active agent and water were 4.0 parts and 29.3 parts, respectively, per 100 parts of the organopolysiloxane.

The volume-average particle diameter of the organopolysiloxane particles was about 25 μm and the distribution of the volume-average particle diameter followed approximately a normal distribution with the value of the parameter α equal to 0.43. The storage stability of the emulsion was rated B.

EXAMPLE 4

The procedure for the preparation of a fourth oil-in-water organopolysiloxane emulsion composition was substantially the same as in Example 3 excepting for the replacement of 13.3 parts of the 30% by weight aqueous solution of lauryl trimethyl ammonium chloride with the same amount of a 64% by weight aqueous solution of stearyl trimethyl ammonium chloride. The total amounts of the cationic surface active agent and water were 8.5 parts and 24.8 parts, respectively, per 100 parts of the organopolysiloxane.

The volume-average particle diameter of the organopolysiloxane particles was about 45 μm and the distribution of the volume-average particle diameter followed approximately a normal distribution with the value of the parameter α equal to 0.75. The storage stability of the emulsion was rated B.

EXAMPLE 5

The procedure for the preparation of a fifth oil-in-water organopolysiloxane emulsion composition was substantially the same as in Example 2 excepting for the replacement of the organopolysiloxane in Example 2 with the same amount of a second organopolysiloxane having a viscosity of 1,000,000 centipoise, which was a 40:60 by weight mixture of a dimethylpolysiloxane having a viscosity of 7,000,000 centipoise and a dimethylpolysiloxane having a viscosity of 100 centipoise. The total amounts of the cationic surface active agent and water were 6.0 parts and 27.3 parts, respectively, per 100 parts of the organopolysiloxane.

The volume-average particle diameter of the organopolysiloxane particles was about 32 μm and the distribution of the volume-average particle diameter followed approximately a normal distribution with the value of the parameter α equal to 0.58. The storage stability of the emulsion was rated A.

EXAMPLE 6

The procedure for the preparation of a sixth oil-in-water organopolysiloxane emulsion composition was about the same as in Example 1 excepting for the replacement of the organopolysiloxane with the same amount of a third organopolysiloxane having a viscosity of 30,000 centipoise, which was a 20:80 by weight mixture of a dimethylpolysiloxane having a viscosity of 15,000,000 centipoise and decamethyl cyclopentasiloxane, decrease in the amount of the aqueous solution of the cationic surface active agent from 26.7 parts to 7.1 parts and increase in the amount of water for dilution of the base emulsion from 6.7 parts to 35.7 parts. The total amounts of the cationic surface active agent and water were 2.1 parts and 40.7 parts, respectively, per 100 parts of the organopolysiloxane.

The volume-average particle diameter of the organopolysiloxane particles was about 15 μm and the distribution of the volume-average particle diameter followed approximately a normal distribution with a value of the parameter α equal to 0.38. The storage stability of the emulsion was rated A.

EXAMPLE 7

The procedure for the preparation of a seventh oil-in-water organopolysiloxane emulsion composition was about the same as in Example 1 except that the initial charge to the emulsifying machine consisted of 100 parts of a dimethylpolysiloxane having a viscosity of 100,000 centipoise and 13.3 parts, instead of 26.7 parts, of the same aqueous solution of the cationic surface active agent and replacement of 6.7 parts of water for dilution of the base emulsion with 20.0 parts of a 30% by weight aqueous solution of cetyl trimethyl ammonium chloride. The total amounts of the cationic surface active agent and water were 10.0 parts and 23.3 parts, respectively, per 100 parts of the organopolysiloxane.

The volume-average particle diameter of the organopolysiloxane particles was about 15 μm and the distribution of the volume-average particle diameter followed approximately a normal distribution with a value of the parameter α equal to 0.36. The storage stability of the emulsion was rated A.

EXAMPLE 8

The procedure for the preparation of an eighth oil-in-water organopolysiloxane emulsion composition was about the same as in Example 1 except that the base emulsion by phase inversion was prepared from 100 parts of the same dimethylpolysiloxane having a viscosity of 100,000 centipoise as used in Example 7 and 21.4 parts of the same aqueous solution of the cationic surface active agent as used in Example 3 and the base emulsion was diluted by the addition of 7.1 parts of the same aqueous solution of the cationic surface active agent and 14.3 parts of purified water in combination. The total amounts of the cationic surface active agent and water were 8.6 parts and 34.3 parts, respectively, per 100 parts of the organopolysiloxane.

The volume-average particle diameter of the organopolysiloxane particles was about 30 μm and the distribution of the volume-average particle diameter followed approximately a normal distribution with a value of the parameter α equal to 0.52. The storage stability of the emulsion was rated B.

EXAMPLE 9

The procedure for the preparation of a ninth oil-in-water organopolysiloxane emulsion composition was about the same as in Example 8 except that the base emulsion by phase inversion was prepared from 100 parts of a dimethylpolysiloxane having a viscosity of 1,000,000 centipoise and 21.4 parts of the same aqueous solution of the cationic surface active agent as used in Example 8 and the base emulsion was diluted by the addition of 21.4 parts of purified water. The total amounts of the cationic surface active agent and water were 6.4 parts and 36.4 parts, respectively, per 100 parts of the organopolysiloxane.

The volume-average particle diameter of the organopolysiloxane particles was about 30 μm and the distribution of the volume-average particle diameter followed approximately a normal distribution with a value of the parameter α equal to 0.48. The storage stability of the emulsion was rated B.

Comparative Example 1

A base emulsion was prepared from 100 parts of the same organopolysiloxane as used in Example 1 and 0.6 part of the same aqueous solution of the cationic surface active agent as used in Example 1 but no phase inversion took place in the emulsion. The base emulsion was diluted by the addition of 21.4 parts of the same aqueous solution of the cationic surface active agent as above and 20.9 parts of purified water in combination. The total amounts of the cationic surface active agent and water were 6.6 parts and 36.3 parts, respectively, per 100 parts of the organopolysiloxane.

No stable aqueous emulsion could be obtained so that the particle size measurement was not undertaken. Storage stability of the emulsion was rated C as a matter of course.

Comparative Example 2

The procedure for the preparation of a second comparative oil-in-water organopolysiloxane emulsion composition was substantially the same as in Example 1 excepting for an increase in the amount of the same aqueous solution of the cationic surface active agent from 26.7 parts to 55.0 parts in the preparation of the base emulsion and an increase in the amount of water for dilution of the base emulsion from 6.7 parts to 11.7 parts. The total amounts of the cationic surface active agent and water were 16.5 parts and 50.2 parts, respectively, per 100 parts of the organopolysiloxane.

The volume-average particle diameter of the organopolysiloxane particles was about 110 μm and the value of the parameter α in the particle size distribution was 1.2. The storage stability of the emulsion was rated C.

Comparative Example 3

The procedure for the preparation of a third comparative aqueous emulsion of organopolysiloxane was substantially the same as in Example 4 excepting for an increase of the amount of the same aqueous solution of cationic surface active agent from 13.3 parts to 50.0 parts in the preparation of the base emulsion and a decrease in the amount of water for dilution of the base emulsion from 20.0 parts to 16.7 parts. The total amounts of the cationic surface active agent and water were 32.0 parts and 34.7 parts, respectively, per 100 parts of the organopolysiloxane.

The volume-average particle diameter of the organopolysiloxane particles was about 150 μm and the value of the parameter α in the particle size distribution was 1.5. The storage stability of the emulsion was rated C.

What is claimed is:

1. An oil-in-water aqueous organopolysiloxane emulsion composition as a uniform dispersion which comprises:
    (A) 100 parts by weight of an organopolysiloxane having a viscosity in the range from 100 to 5,000,000 centipoise at 25° C. and represented by the average unit formula $$R_a SiO_{(4-a)/2},$$

in which R denotes a monovalent organic group having 1 to 20 carbon atoms and the subscript a is a positive number in the range from 1.8 to 2.2;
    (B) from 0.5 to 30 parts by weight of a cationic surface active agent which is a quaternary ammonium compound represented by the general formula $$[R^1_4 N]^+ \cdot X^-,$$

which at least one of the four groups denoted by $R^1$ is an alkyl or alkenyl group having 8 to 28 carbon atoms, each of the remaining groups denoted by $R^1$, if any, is, independently from the others, a benzyl group or an alkyl group having 1 to 5 carbon atoms and $X^-$ denotes a halogen anion or an organic anion; and
    (C) from 10 to 300 parts by weight of water as a dispersion medium of the components (A) and (B),
    the component (A) being uniformly dispersed in the component (C) in the form of particles having a volume-average particle diameter in the range from 3 to 100 μm.

2. The oil-in-water aqueous organopolysiloxane emulsion composition as claimed in claim 1 in which the group denoted by R is a monovalent hydrocarbon group.

3. The oil-in-water aqueous organopolysiloxane emulsion composition as claimed in claim 2 in which all of the monovalent hydrocarbon groups denoted by R are methyl groups or a combination of methyl groups and phenyl groups of which at least 50% by moles are methyl groups.

4. The oil-in-water aqueous organopolysiloxane emulsion composition as claimed in claim 1 in which the organopolysiloxane as the component (A) has a viscosity in the range from 1000 to 3,000,000 centipoise at 25° C.

5. The oil-in-water aqueous organopolysiloxane emulsion composition as claimed in claim 4 in which the organopolysiloxane as the component (A) is a mixture of a first organopolysiloxane having a viscosity in the range from 10 to 100 centipoise at 25° C. and a second organopolysiloxane having a viscosity in the range from 5,000,000 to 2,000,000 centipoise at 25° C. in such a proportion that the mixture has a viscosity higher than 1000 but not exceeding 3,000,000 centipoise at 25° C.

6. The oil-in-water aqueous organopolysiloxane emulsion composition as claimed in claim 4 in which the organopolysiloxane as the component (A) has a viscosity in the range from 10,000 to 1,000,000 centipoise at 25° C.

7. The oil-in-water aqueous organopolysiloxane emulsion composition as claimed in claim 6 in which the organopolysiloxane as the component (A) is a mixture of a first organopolysiloxane having a viscosity in the range from 10 to 1000 centipoise at 25° C. and a second organopolysiloxane having a viscosity in the range from 5,000,000 to 2,000,000 centipoise at 25° C. in such a proportion that the mixture has a viscosity in the range from 10,000 to 1,000,000 centipoise at 25° C.

8. The oil-in-water aqueous organopolysiloxane emulsion composition as claimed in claim 1 in which $X^-$ in the general formula representing the cationic surface active agent as the component (B) is a halogen anion.

9. The oil-in-water aqueous organopolysiloxane emulsion composition as claimed in claim 8 in which the cationic surface active agent as the component (B) is selected from the group consisting of cetyl trimethyl ammonium chloride, lauryl trimethyl ammonium chloride and stearyl trimethyl ammonium chloride.

10. The oil-in-water aqueous organopolysiloxane emulsion composition as claimed in claim 1 in which the particles of the organopolysiloxane as the component (A) have a volume-average particle diameter in the range from 10 to 50 μm.

11. The oil-in-water aqueous organopolysiloxane emulsion composition as claimed in claim 1 in which the amount of the cationic surface active agent as the component (B) is in the range from 1 to 20 parts by weight per 100 parts by weight of the organopolysiloxane as the component (A).

12. The oil-in-water aqueous organopolysiloxane emulsion composition as claimed in claim 11 in which the amount of the cationic surface active agent as the component (B) is in the range from 2 to 10 parts by weight per 100 parts by weight of the organopolysiloxane as the component (A).

13. The oil-in-water aqueous organopolysiloxane emulsion composition as claimed in claim 1 in which the amount of water as the component (C) is in the range from 15 to 100 parts by weight per 100 parts by weight of the organopolysiloxane as the component (A).

14. The oil-in-water aqueous, organopolysiloxane emulsion composition as claimed in claim 13 in which the amount of water as the component (C) is in the range from 20 to 50 parts by weight per 100 parts by weight of the organopolysiloxane as the component (A).

15. The oil-in-water aqueous organopolysiloxane emulsion composition of claim 1, wherein the component (A) organopolysiloxane particles have a particle size distribution with a broadness parameter α, defined by the ratio of the standard deviation to the volume-average particle diameter, of 0.1 to 1.0.

16. The oil-in-water aqueous organopolysiloxane emulsion composition of claim 1, wherein the component (A) organopolysiloxane particles are non-volatile.

17. A method for the preparation of an oil-in-water aqueous organopolysiloxane emulsion composition which comprises:

(a) mixing 100 parts by weight of an organopolysiloxane as the component (A) having a viscosity in the range from 100 to 5,000,000 centipoise at 25° C. and represented by the average unit formula $R_aSiO_{(4-a)/2}$, in which R denotes a monovalent organic group having 1 to 20 carbon atoms and the subscript a is a positive number in the range from 1.8 to 2.2, from 0.5 to 30 parts by weight of a cationic surface active agent as the component (B) which is a quaternary ammonium compound represented by the general formula $[R^1_4N]^+X^-$, in which at least one of the four groups denoted by $R^1$ is an alkyl or alkenyl group having 8 to 28 carbon atoms, each of the remaining groups denoted by $R^1$, if any, is, independently from the others, a benzyl group or an alkyl group having 1 to 5 carbon atoms and $X^-$ denotes a halogen anion or an organic anion, and from 1 to 30 parts by weight of water as a part of the component (C) to form an emulsion of the water-in-oil type;

(b) agitating the water-in-oil emulsion to form an oil-in-water base emulsion by phase inversion; and (c) diluting the oil-in-water base emulsion with water as the remaining part of the component (C) in such an amount that the total amount of water made up thereby with the water contained in the base emulsion is in the range from 10 to 300 parts by weight per 100 parts by weight of the organopolysiloxane as the component (A).

18. The method for the preparation of an oil-in-water aqueous organopolysiloxane emulsion composition as claimed in claim 17 in which the amount of water added to the base emulsion in step (c) is at least 20% of the water contained in the base emulsion.

19. The method for the preparation of an oil-in-water aqueous organopolysiloxane emulsion composition as claimed in claim 18 in which the amount of water added to the base emulsion in step (c) is at least 30% of the water contained in the base emulsion.

20. The method for the preparation of an oil-in-water aqueous organopolysiloxane emulsion composition as claimed in claim 17 in which the cationic surface active agent as the component (B) mixed in step (a) with the organopolysiloxane as the component (A) is in the form of an aqueous solution.

21. The method for the preparation of an oil-in-water aqueous organopolysiloxane emulsion composition as claimed in claim 17 in which the oil-in-water base emulsion is diluted in step (c) with water containing an additional amount of a cationic surface active agent dissolved therein in such an amount that the total amount of the cationic surface active agent used in step (a) and the additional amount of the cationic surface active agent is in the range from 0.5 to 30 parts by weight per 100 parts by weight of the organopolysiloxane as the component (A).

22. The method for the preparation of an oil-in-water aqueous organopolysiloxane emulsion composition as claimed in claim 17 in which the amount of water used in step (a) is in the range from 5 to 20 parts by weight per 100 parts by weight of the organopolysiloxane as the component (A).

23. The method for the preparation of an oil-in-water aqueous organopolysiloxane emulsion composition as claimed in claim 17 in which the agitation of the emulsion in step (b) is performed at a temperature in the range from 0° to 50° C.

24. The method for the preparation of an oil-in-water aqueous organopolysiloxane emulsion composition as claimed in claim 17 in which the phase inversion of the emulsion in step (b) is followed by further continued agitation for 30 minutes to 2 hours at a temperature in the range from 0° to 50° C.

25. The method of claim 17, wherein the oil-in-water aqueous organopolysiloxane emulsion composition of step (c) contains the component (A) organopolysiloxane uniformly dispersed in the component (C) water in the form of particles having a volume-average particle diameter in the range from 3 to 100 μm.

26. The method of claim 17, wherein the oil-in-water aqueous organopolysiloxane emulsion composition of step (c) has component (A) organopolysiloxane particles with a particle size distribution having a broadness parameter α, defined by the ratio of the standard deviation to the volume-average particle diameter, of 0.1 to 1.0.

27. The method of claim 17, wherein the oil-in-water aqueous organopolysiloxane emulsion composition from step (c) has component (A) organopolysiloxane particles which are non-volatile.

* * * * *